United States Patent [19]

Garzia et al.

[11] Patent Number: 4,950,669
[45] Date of Patent: Aug. 21, 1990

[54] METHODS AND COMPOSITIONS FOR PROMOTING GROWTH OF ANIMALS

[75] Inventors: Aldo Garzia; Umberto Bucci, both of Milan, Italy

[73] Assignee: Cometec s.r.l., Milan, Italy

[21] Appl. No.: 221,362

[22] Filed: Jul. 19, 1988

[30] Foreign Application Priority Data

Jul. 20, 1987 [IT] Italy ............................... 21356 A/87
Jun. 17, 1988 [IT] Italy ............................... 48093 A/88

[51] Int. Cl.$^5$ ............................................ A61K 31/535
[52] U.S. Cl. ............................... 514/237.5; 514/559; 514/545; 514/532; 514/467; 514/621; 514/255; 514/330
[58] Field of Search .................................. 514/237.5

[56] References Cited

U.S. PATENT DOCUMENTS

| | | | |
|---|---|---|---|
| 3,239,345 | 3/1966 | Hodge et al. | 99/2 |
| 4,115,570 | 9/1978 | Garzia et al. | 424/248.57 |
| 4,128,642 | 12/1978 | Ivy et al. | 424/251 |
| 4,753,937 | 6/1988 | Garzia et al. | 514/231.5 |

FOREIGN PATENT DOCUMENTS 1305138 1/1973 United Kingdom .

OTHER PUBLICATIONS

Koo, *J. Am. Chem. Soc.*, 75:720 (1953).
Garzia et al., *Riv. di Farm.* V: 323–326 (1974).

*Primary Examiner*—Frederick E. Waddell
*Attorney, Agent, or Firm*—Bernard, Rothwell & Brown

[57] ABSTRACT

The growth rate of an animal is stimulated by administering to the animal a growth promoting amount of a compound of the formula

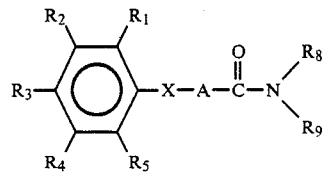

wherein $R_1$, $R_2$, $R_3$, $R_4$ and $R_5$, which can be the same or different, are each selected from the group consisting of hydrogen, alkyl having 1 to 4 carbon atoms, alkoxy having 1 to 4 carbon atoms and halogen; X is selected from carbonyl and a ketal group of the formula

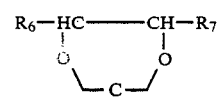

wherein $R_6$ and $R_7$, which can be the same or different, are each selected from hydrogen and alkyl having 1 to 3 carbon atoms; A is a linear or branched alkylene having from 1 to 8 carbon atoms; and $R_8$ and $R_9$, which can be the same or different, are each selected from the group consisting of hydrogen, alkyl having 1 to 4 carbon atoms, or 2-hydroxy-alkyl wherein the alkyl group has 2 to 4 carbon atoms, or $R_8$ and $R_9$, together with the nitrogen atom, form a heterocyclic ring optionally including other heteroatoms; provided that, when X is a ketal group and A is ethylene, the radical

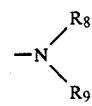

is a group other than morpholino.

7 Claims, No Drawings

METHODS AND COMPOSITIONS FOR PROMOTING GROWTH OF ANIMALS

BACKGROUND OF THE INVENTION

1. Field of the Invention

This invention relates to injectable or oral compositions for increasing the growth rate of animals such as swine, cattle, sheep and poultry. The invention also relates to feed compositions containing additives that promote increased growth rates in animals.

2. Prior Art

It is an objective of the meat production industry to stimulate the growth rate of animals. A number of substances have been administered for the purpose of increasing growth rates. For example, it is known that certain compounds having estrogenic activity can be used for this purpose. These compounds, however, sometimes produce serious undesirable side effects.

A variety of other substances are currently being used as animal growth promotants. For promoting growth in swine, for example, quinoxaline compounds can be used, as described by Haddadin et al. (British Patent No. 1,305,138), by R. E. Ivy and R. D. Williams (U.S. Pat. No. 4,128,642) and others. U.S. Pat. No. 3,239,345 to Hodge et al. discloses the use of zearalanol as a growth promoting agent in cattle and sheep. Derivatives of the antibiotic Bacitracin are used as growth-promoting agents in chickens.

With regard to the quinoxalines, antibiotics and their derivatives, the growth stimulating effects of these substances result primarily from the generally improved health status of the animals are not from improved feed conversion. Furthermore, there has been a considerable concern that the widespread use of these compounds for growth promotion may result in the widespread increase in antibiotic-resistant strains of undesirable bacteria through the pressure of natural selection.

Another disadvantage of currently used growth stimulants is that they frequently are active only in limited species, in some cases only in a single animal species.

There is a need for growth-promoting agents which do not have disadvantages associated with prior art growth promotants and which can be used in a variety of species with satisfactory results.

SUMMARY OF THE INVENTION

In accordance with the present invention, there are provided compositions for promoting the growth of an animal, containing as active principle one or more compounds of formula I:

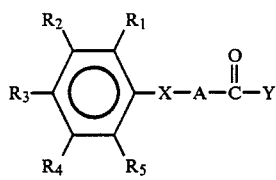

wherein $R_1$, $R_2$, $R_3$, $R_4$ and $R_5$, which can be the same or different, are each selected from the group consisting of hydrogen, alkyl having 1 to 4 carbon atoms, alkoxy having 1 to 4 carbon atoms and halogen;

X is selected from carbonyl and a ketal group of the formula:

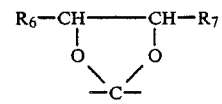

wherein $R_6$ and $R_7$, which can be the same or different, are each selected from hydrogen and alkyl having 1 to 3 carbon atoms;

A is a linear or branched alkylene having from 1 to 8 carbon atoms;

Y is selected from OQ (wherein Q is selected from hydrogen, alkyl having 1 to 4 carbon atoms, a cation of an alkali or earth alkali metal and a cation of a nontoxic organic base); and a group of formula:

wherein $R_8$ and $R_9$, which can be the same or different, are each selected from the group consisting of hydrogen, alkyl having 1 to 4 carbon atoms and 2-hydroxyalkyl having 2 to 4 carbon atoms; or $R_8$ and $R_9$, together with the nitrogen atom, form a heterocyclic ring optionally including other heteroatoms; provided that, when X is a ketal group and A is ethylene, the group $NR_8R_9$ is a group other than morpholino.

Preferred compounds according to the invention are compounds of formula I wherein $R_1$, $R_2$, $R_3$, $R_4$ and $R_5$ are hydrogen; X is the carbonyl group; A is a linear alkylene having 1-2 carbon atoms; Y is $NR_8R_9$ wherein both $R_8$ and $R_9$ are 2-hydroxyalkyl having 2-4 carbon atoms, or $NR_8R_9$ is a morpholino, piperidino or piperazino group; or Y is OQ, wherein Q is the cation of morpholine, piperidine or piperazine.

The most preferred compound according to the invention is N-morpholinyl-β-benzoyl-propionamide (formula I wherein $R_1$, $R_2$, $R_3$, $R_4$ and $R_5$ are hydrogen, X=CO, A=$CH_2CH_2$ and

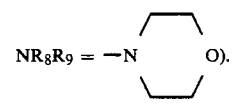

Another object of the invention are compounds of formula I wherein $R_1$ to $R_5$, X, A and Y have the above specified meanings, provided that:

(1) when X=CO and each of $R_1$-$R_5$, independently, is either a hydrogen or an alkoxy group,
  (a) $R_8$ and $R_9$ are not a combination of hydrogen and an alkyl group or two alkyl groups, and the group —$NR_8R_9$ is not morpholino; and
  (b) Q has to be different from hydrogen, methyl and ethyl;

(2) when X=ketal and each of $R_1$-$R_5$, independently, is a hydrogen, an alkyl group or an alkoxy group, the group —$NR_8R_9$ is a group other than morpholino.

DETAILED DESCRIPTION OF THE INVENTION

We have found that the compounds of formula I are capable of stimulating growth in a variety of animal species without exhibiting undesirable activities. The compounds exhibit very low toxicity. They are metabolized rapidly and the metabolites have a minimal toxicity.

A number of the compounds of formula I in which X is carbonyl, including the most preferred compound, N-morpholinyl-$\beta$-propionamide, are disclosed by Aldo Garzia et al. in "Rivista di Farmacologia e Terapia" V, 323,326 (1974) and U.S. Pat. No. 4,115,570, issued to Aldo Garzia. The compounds are disclosed as central nervous system depressants.

Compounds of formula I in which X is carbonyl and Y=$NR_8R_9$ can be obtained by methods disclosed in U.S. Pat. No. 4,115,570. In particular, they can be prepared from benzoyl alkanoic acids or acid halides of the formula

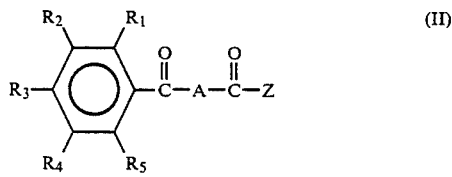

wherein A, $R_1$, $R_2$, $R_3$, $R_4$ and $R_5$ are as previously described and Z is —OH or halogen, e.g., chlorine.

The benzoyl alkanoic acids, for instance, $\beta$-benzoyl propionic acid, can be prepared by the reaction of a corresponding alkyl benzoylacetate with alkyl $\beta$-bromopropionate in the presence of sodium at low temperature, e.g., 0° C., followed by hydrolysis of the crude ester with sulfuric acid. The acid halide can be prepared for the corresponding acid by conventional procedures, for instance, by reaction with thionyl chloride, oxalyl chloride, or the like.

A compound of formula I in which X is a carbonyl group and Y is $NR_8R_9$ can be prepared by reacting a compound of formula II with an amine compound of the formula $R_8$—NH—$R_9$, e.g. morpholine. When proceeding with the benzoyl alkanoic acid route of synthesizing the compounds of formula I, which is the preferred route of synthesis, the benzoyl alkanoic acid may be converted to an acid anhydride as an intermediate, then reacted with the amine to provide the compound of formula I. The acid anhydride may be prepared by reacting the benzoyl alkanoic acid with an alkyl ester of a haloformate (i.e., halocarbonate), particularly a chloroformate. The alkyl ester may be a lower alkyl ester, with ethyl chloroformate and isobutyl chloroformate being preferred. The reaction proceeds at room temperature; however, higher or lower reaction temperatures may be employed. The reaction temperature should not be so low as to unduly slow the reaction rate or so high as to lead to the deterioration of the starting materials or products. Often a temperature of about 0° to 50° C. or more may be used. The reaction produces a hydrogen halide byproduct. A hydrogen halide acceptor, such as a tertiary amine may be employed. A preferred hydrogen halide acceptor is triethylamine. Triethylamine hydrochloride, for instance, will precipitate out from a benzene menstruum. The reaction is preferably conducted under essentially anhydrous conditions and in the presence of an inert organic solvent, for instance, benzene, toluene, and the like.

The intermediate compound, or mixed acid anhydride, may be represented by the formula

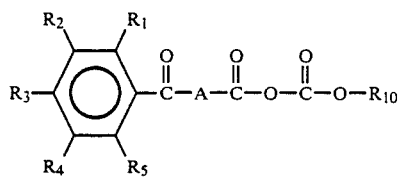

wherein A, $R_1$, $R_2$, $R_3$, $R_4$ and $R_5$ are as defined above and $R_{10}$ is lower alkyl The mole ratio of benzoyl alkanoic acid to alkyl haloformate may range widely; although, since the alkyl haloformate may often be more readily obtained, it may be employed in excess of that required for completion of the reaction on a stoichiometric basis.

Frequently, the mole ratio of benzoyl alkanoic acid to alkyl haloformate may be about 0.1:1 to 5:1, preferably about 0.5:1 to 1.1:1. The hydrogen halide acceptor may also be employed in widely varying amounts, preferably in a mole ratio to the benzoyl alkanoic acid of about 0.1:1 to 10:1, more preferably about 0.8 to 1.5:1. The solvent may be provided in solvent-providing quantities, for instance, about 5 to 1000 milliliters per gram of benzoyl alkanoic acid.

It is generally preferably to add the compound $R_8$-NH-$R_9$ to the reaction mixture subsequent to the addition of the alkyl haloformate. The reaction proceeds at room temperature, although higher and lower temperatures may be employed under the same constraints as those for the preparation of the mixed acid anhydride.

Often, a temperature of about 0° to 50° C. or more is employed. The amine is preferably employed in excess of that required for reaction on a stoichiometric basis with the benzoyl alkanoic acid. The mole ratio of benzoyl alkanoic acid to amine can be about 1:1.5 to 1:20, preferably about 1:2 to 1:3. The reaction proceeds quickly, particularly under agitation, and the reaction is normally substantially complete in about 0.01 to 50 hours at room temperature.

The compound of formula I wherein X is a carbonyl group and Y is —$NR_8R_9$ may be recovered by conventional means, for instance, by filtering out the hydrogen halide acceptor; washing the organic phase; neutralizing, if desired, with, for instance, sodium bicarbonate; concentrating, e.g., by evaporation; and separating, and then recrystallizing the product from solvent.

In the process of preparing the compounds of formula I (wherein X=CO and Y=—$NR_8R_9$) in which the acid halide is employed as a starting material, the reaction with the amine can be conducted in the presence of a base, for instance, an alkali metal base, such as sodium hydroxide or potassium hydroxide, or pyridine, at ambient temperatures. Temperatures of about 0° to 100° C. may be used. The base serves as a halide acceptor. The mole ratio of acid halide to amine can be in the range of about 0.1:1 to 10:1 and the mole ratio of acid halide to base may being the range of about 0.1:1 to 10:1. The reaction may be conducted in an inert solvent such as benzene, toluene or the like.

The compounds of formula I in which X is carbonyl and Y=—$NR_8R_9$ can also be produced by reacting the amine directly with the compounds of formula II in the presence of dicyclohexylcarbodiimide in an anhydrous solvent such as anhydrous tetrahydrofuran. The amine, the compound of formula II and dicyclohexylcarbodiimide are employed in equimolar amounts. The reaction is carried out at boiling temperature.

Compounds of formula I wherein Q is an inorganic or organic cation are prepared by reacting the acids (I, wherein Y=OH) with the corresponding bases in an alcoholic medium, optionally in a mixture of a $C_1$-$C_3$ alcohol and a lower ketone or ether. The so obtained salts are generally insoluble in lower ethers and aromatic hydrocarbons, scarcely soluble in alcohols and soluble in water.

Compounds of formula I in which X is ketal group can be prepared by reacting the analogous compounds in which X is carbonyl with 1,2-glycols such as ethylene glycol, propylene glycol, etc. The reaction is preferably carried out in a suitable solvent such as benzene at boiling temperature for about 50 hours, in the presence of a catalyst such as p-toluene sulfonic acid monohydrate. The presence of a large excess of glycol is essential, the reaction is facilitated by removal of water formed while the reaction is in progress.

The compound of formula I is administered to animals to promote growth. The compound is capable of increasing the growth rates of single-stomached, ruminant and avian species including swine, poultry, cattle and sheep. The ratio of meat/fat/none remains unchanged in animals treated with the compound.

Animals can be treated with the compound of formula I by any means conventionally employed to administer growth promotants, for example, by parenteral administration, e.g., intramuscular (i.m.) injection; orally (p.o.); or by means of the subcutaneous implantation of a controlled release device containing the compound.

In the case of parenteral administration, the compound of formula I is generally employed in conjunction with a sterile liquid carrier vehicle. Suitable liquid carrier vehicles include, for example, pharmaceutically acceptable poly(alkylene oxides), e.g., polyethylene glycols and polypropylene glycols, phosphate buffered saline, etc. Intramuscular injection is a preferred route of parenteral administration. The compound of formula I is preferably present at a concentration from about 1% to 15%. A preferred carrier vehicle is polyethylene glycol. For i.m. administration, we have found that about a 2% solution of N-morpholinyl-$\beta$-benzoyl-propionamide is most preferred. A suitable single parenteral dosage for an animal is from about 1.0 mg/kg to about 2.5 mg/kg, based on the body weight of the animal. Injections are administered when treatment is initiated, and thereafter, at approximately 15-day intervals.

When administering the compound of formula I orally, the dosage can be 10 times or more that which is administered parenterally. Suitable dosage forms for oral administration include pills, lozenges, tablets, capsules, dry powder as a premix or liquid suspensions in any of the known pharmaceutically acceptable carriers. A preferred method of oral administration comprises admixing the compound of formula I with the animal's feed. Preferably, the compound of formula I is admixed with the animal feed in an amount from about 1 mg to about 60 mg per kilogram of feed.

Through a series of tests it has been found that the formula I compounds exhibit extremely low toxicity in relation to the dosage used; for the N-morpholinyl-$\beta$-propionamide, the $LD_{50}$ in the mouse for i.p. administration is 940 mg/kg (safe limits 648-1363 mg/kg). Per os, in the mouse still, the $LD_{50}$ is above 2000 mg/kg. In the rat, after i.p. treatment with 50 mg/kg there was, within 3 hours from administration, a maximum lowering of the body temperature of 0.6° in respect to the controls treated with the only suspending medium. In rabbits treated with 100 mg/kg of i.p. compound, after 300 minutes of observation, there were no electrocardiographic variations compared to the controls.

At the same dosage (always by i.p. administration) the compound is not hypotensive in the awake rabbit.

After per os treatment with 300 mg/kg, in the rat, the organs of the treated animals showed the following weight variations (in %):

|  | Treated animals | Controls |
|---|---|---|
| suprarenal gland | +0.011 | +0.011 |
| lung | +0.675 | +0.598 |
| heart | +0.304 | +0.257 |
| liver | +3.63 | +3.22 |
| kidney | +0.71 | +0.65 |

Treatment with the compound of formula I does not preclude--and is compatible with--drug therapy, e.g., antibiotics, vitamins, etc. The treated animals are specifically resistant to stress during transport, changes in weather or stabling.

The following examples are intended to illustrate further the practice of the invention and are not intended to limit its scope in any way.

EXAMPLE I

A suspension of 17.8 grams (0.1 mole) of $\beta$-benzoyl-propionic acid (*Organic Synthesis*, 2:81) in 500 milliters of dry benzene is prepared and 10.5 grams of triethylamine, 15 grams of ethyl chloroformate, and 18 grams (0.2 mole) of morpholine are sequentially added. The suspension is stirred for two hours at room temperature and then filtered to remove the precipitated triethylamine hydrochloride. The mother liquor is evaporated in a small amount for filtration and the solid product which is obtained, is separated by filtration and crystallized from ethanol to provide about 15 grams of N-morpholinyl-$\beta$-benzoyl-propionamide having a melting point of 87°-89° C.

EXAMPLE II

A suspension of 14 grams (0.05 mole) of 3,4,5-trimethoxybenzoyl-65 -butyric acid (*J. Am. Chem. Soc.*, 75:720, 1955) in 400 milliliters of dry benzene is prepared and 5.25 grams of triethylamine are added thereto. To the suspension at room temperature are added 7.5 grams of ethyl chloroformate, thereby providing the mixed acid anhydride. When the addition the ethyl chloroformate is complete, 9 grams (0.1 mole) of morpholine are added and the mixture is stirred for two hours, then filtered to remove precipitated triethylamine hydrochloride. The mother liquor is washed with an aqueous sodium bicarbonate solution and then concentrated by evaporation to a small volume to provide a solid product and sufficient liquid for filtration, e.g., about 20 to 40 milliliters. Solid product which is obtained is crystallized from methanol to provide about 13 grams of N-morpholinyl-$\gamma$-(3,4,5-trimethoxy-benzoyl)-butyramide having a melting point of 105° to 107° C. This compound can be employed s a growth promotant in a manner similar to that described in examples X-XVII, below.

EXAMPLE III

The procedure of example II is essentially repeated except that 4-methoxybenzoyl-β-propionic acid is used instead of 3,4,5-trimethoxybenzoyl-γ-butyric acid. The product is N-morpholinyl-γ-(4-methoxybenzoyl)propionamide having a melting point of 85° to 87° C. This compound can be employed as a growth promotant, in a manner similar to that described in examples X-XVII, below.

EXAMPLE IV

The procedure of example II is essentially repeated except that 4-methoxybenzoyl-γ-butyric acid is used instead of 3,4,5-trimethoxybenzoyl-γ-butyric acid. The product is N-morpholinyl-γ-(4-methoxybenzoyl)-butyramide having a melting point of 92° to 93° C. This compound can be employed as a growth promotant in a manner similar to that described in examples X-XVII, below.

EXAMPLE V

A solution is prepared containing 17.8 grams (0.1 mole) β-benzoyl-propionic acid in 500 ml of anhydrous tetrahydrofuran. There are then added 20.7 grams (0.1 mole) dicyclohexylcarbodiimide and 9.8 grams (0.2 mole) morpholine. The reactants are reacted at reflux for 30 hrs. The reaction mixture is allowed to cool. The cooled mixture is filtered and the filtrate is concentrated to about one-fifth its initial volume. After vacuum drying, there are obtained 19.5 grams of crystalline N-morpholinyl-β-benzoyl-propionamide having a melting point of 88°-89° C.

EXAMPLE VI

N,N-bis(2-hydroxyethyl)-β-benzoyl-propionamide

A suspension is prepared containing 17.8 grams (0.1 mole)-β-benzoyl-propionic acid in 500 ml of anhydrous benzene; then are added in this order and at room temperature 10.5 grams triethylamine, 15 grams ethyl chlorocarbonate and 21 grams (0.2 moles) diethanolamine. The suspension is stirred for over two hours, always at room temperature, and it is then filtered to remove the triethylamine hydrochloride. The liquid is concentrated, at reduced pressure, to about half of the initial volume and it is left to rest about 12 hours at 5°-10° C. temperature. The crystallized solid is filtered, vacuum dried at reduced pressure, about 40° C., and is recrystallized from ethanol. 17.5 grams of N,N-bis(2- hydroxyethyl)-β-benzoyl-propionamide with m.p. 98° C. are obtained.

The I.R. and N.M.R. spectra confirm the structure corresponding to the title.

EXAMPLE VII

To the stirred solution of 17.89 grams (0.1 mole) of β-benzoylpropionic acid in 50 milliliters of absolute ethanol, 8.7 grams (0.1 mole) of pure morpholine are added. The morpholine salt of β-benzoyl propionic acid is separated by filtration and washed with dry diethyl ether. Yield 78%; m.p. 150°-53° C. (with decomposition).

Elementary analysis: for $C_{14}H_{19}NO_4$ (MW 265.31): Calc. % C 63.38; H 7.22; N 5.28: found % C 63.23; H 7.27; N 5.21.

By the same procedure the following salts of β-benzoylpropionic acid are obtained:

piperidine salt, m.p. 162°-64° C.;
N,N'-dibenzyl-ethylenediamine salt, m.p. 158°-61° C.;
N-methylpiperazine salt, m.p. 176°-177° C.

EXAMPLE VIII

A suspension of 3.7 grams (0.05 mole) of pure calcium hydroxide in 30 milliliters of distilled water is prepared; under stirring 19.1 grams (0.1 mole) of γ-benzoylbutyric acid are added. The mixture is heated to 40° C., then 30 milliliters of ethanol are added and the suspension is cooled to 10° C. By filtration and washing with ethanol the calcium salt is obtained in a yield of about 90%; decomposition occurs at 160° C.

By the same procedure the magnesium and zinc salts are prepared.

EXAMPLE IX

The procedure of example VII is essentially repeated except that β-benzoylbutyric acid is used instead of β-benzoylpropionic acid, and N-methylglucamine instead of morpholine. The obtained salt melts at 138°-40° C. with decomposition.

EXAMPLE X

N-morpholinyl-β-benzoylpropionamide (NMBP) was formulated as an injectable product at a concentration of 2% in polyethylene glycol. The formulation was administered to pigs by intramuscular injection at a dosage of 1 mg/kg, once every seven days. Pigs averaged 52.66 kg at initiation and were terminated at 90.8 kg. Control animals received no injections. The average daily gain (ADG) in kg, average daily feed consumption (ADF) in kg and feed-to-gain ratio (F/G) are presented in Table I. The results indicate that average daily gain was improved about 10% and feed-to-gain ratio was improved about 4% for the treated animals as compared with controls.

TABLE I

| Treatment | No. of Pigs | ADG | ADF | F/G |
|---|---|---|---|---|
| Control | 11 | 0.867 | 2.76 | 3.18 |
| NMBP | 12 | 0.958 | 2.96 | 3.03 |

EXAMPLE XI

N-morpholinyl-β-benzoyl-propionamide was admixed with swine feed at 20 ppm and at 60 ppm. A six-week feeding study was conducted using weanling barrows. Pigs averaging 8.80 kg initially (4–5 weeks of age) were housed four pigs per pen. Test diets were fed ad libitum throughout the six-week study. Average final weight for all pigs was 27.33 kg. Results of the study are presented in Table II.

TABLE II

| Parameter | 1 | 2 | 3 |
|---|---|---|---|
| Avg. daily gain | | | |
| (kg) | 0.42 | 0.45 | 0.42 |
| (rel.) | 100 | 108 | 100 |
| daily feed | | | |
| (kg) | 0.996 | 1.022 | 0.96 |
| (rel.) | 100 | 107 | 101 |
| (kg) | 2.30 | 2.26 | 2.34 |

TABLE II-continued

| Parameter | 1 | 2 | 3 |
|---|---|---|---|
| (rel.) | 100 | 98 | 102 |

1 Control
2 NMBP, 20 ppm
3 NMBP, 60 ppm

EXAMPLE XII

Portions of N-morpholinyl-$\beta$-benzoyl-propionamide were admixed with chicken feed at 1 mg/kg and a 2 mg/kg, respectively. Another portion was formulated into an injectable formulation at a concentration of 2% in polyethylene glycol. The N-morpholinyl-$\beta$-benzoyl-propionamide was then administered to chickens, either by i.m. injection or in feed, over 28-day period. One group of controls received no medication, while another group of controls received Bacitracin MD in its feed at 30 g/ton. Those chickens receiving intramuscular injections were injected once a week with a dosage of either 1 mg/kg or 2 mg/kg, based on body weight. Birds were weighed on days 0, 14 and 28. Results are presented in Table III.

TABLE III

| Treatment | Average Weight (g) | | | Weight Gain (g) | | Feed Conversion | |
|---|---|---|---|---|---|---|---|
| | Day 0 | Day 14 | Day 28 | Day 14 | Day 28 | Day 14 | Day 28 |
| Control | 98.4 | 474.2 | 1012.0 | 375.8 | 913.6 | 1.39 | 1.58 |
| Feed 1 mg/kg | 98.9 | 462.8 | 947.6 | 363.9 | 848.7 | 1.38 | 1.64 |
| Feed 2 mg/kg | 98.5 | 474.3 | 1013.5 | 375.8 | 915.0 | 1.38 | 1.56 |
| Injection 1 mg/kg | 98.7 | 460.6 | 938.2 | 361.9 | 839.5 | 1.37 | 1.61 |
| Injection 2 mg/kg | 98.6 | 456.3 | 971.4 | 357.7 | 872.8 | 1.38 | 1.56 |
| Bacitracin MD | 98.6 | 475.6 | 1026.9 | 377.0 | 928.3 | 1.37 | 1.58 |

EXAMPLE XIII

N-morpholinyl-$\beta$-benzoyl-propionamide was admixed with chicken feed at concentrations of 1.0 ppm, 7.5 ppm and 15 ppm. A 21-day battery study was conducted with the NMBP-containing feed. One group of controls was unmedicated, while a second control group received Bacitracin MD in its feed at 30 g/ton. The birds were fed ad libitum and weighed on days 7, 14 and 21. There were 10 birds per replication, 4 replications in controls and 2 replications per drug treatment. Results are presented in Table IV.

TABLE IV

| | Day 7 | | Day 14 | | Day 21 | |
|---|---|---|---|---|---|---|
| Medication | Weight Gain (g) | F/G | Weight Gain (g) | F/G | Weight Gain (g) | F/G |
| Control | 327 | 1.45 | 682 | 1.53 | 1056 | 1.62 |
| NMBP 1 ppm | 341 | 1.38 | 715 | 1.47 | 1152 | 1.62 |
| NMBP 7.5 ppm | 325 | 1.40 | 697 | 1.49 | 1113 | 1.60 |
| NMBP 15 ppm | 318 | 1.42 | 688 | 1.47 | 1164 | 1.54 |
| Bacitracin MD 30 g/ton | 337 | 1.37 | 707 | 1.47 | 1155 | 1.58 |

EXAMPLE XIV

A 44-day floor pen study was conducted in which n-morpholinyl-$\beta$-benzoyl-propionamide was administered in chicken feed at concentrations of 1 ppm, 2.5 ppm, 5 ppm, 10 ppm, 20 ppm, 40 ppm and 60 ppm. One group of controls received no medication in its feed, while a second control group received Bacitracin MD in its feed at 30 g/ton. Birds were fed ad libitum. There were 5 replications per treatment, 50 birds per replication. Birds were weighed to determine weight gain and feed-to-gain ration after 35 days and 44 days. Results are presented in Table V. It can be seen that positive results were obtained with N-morpholinyl-$\beta$-benzoyl-propionamide at feed levels of 2.5 ppm and 5.0 ppm. The lack of positive results normally seen in the bacitracin MD control may be attributed to the fact that the floor-pen house was cleaned and disinfected just prior to the beginning of the study.

TABLE V

| | Day 35 | | Day 44 | |
|---|---|---|---|---|
| Medication | Weight Gain (g) | F/G | Weight Gain (g) | F/G |
| Control | 1364 | 1.61 | 1917 | 1.72 |
| NMBP 1 ppm | 1379 | 1.60 | 1917 | 1.72 |
| NMBP 2.5 ppm | 1431 | 1.55 | 1961 | 1.69 |
| NMBP 5 ppm | 1381 | 1.61 | 1929 | 1.72 |
| NMBP 10 ppm | 1356 | 1.60 | 1883 | 1.74 |
| NMBP 20 ppm | 1364 | 1.61 | 1901 | 1.72 |
| NMBP 40 ppm | 1334 | 1.63 | 1898 | 1.72 |
| NMBP 60 ppm | 1334 | 1.57 | 1875 | 1.72 |
| Bacitracin MD 30 g/ton | 1376 | 1.59 | 1909 | 1.72 |

EXAMPLE XV

In a manner similar to that described in Example XIV, a 44-day floor-pen study was conducted in which N-morpholinyl-$\beta$-benzoyl-propionamide was administered in the chicken feed at concentrations of 1.0 ppm, 2.5 ppm, 5.0 ppm, 10 ppm, 20 ppm, 40 ppm and 60 ppm. There were 60 chickens per replication, 3 replications per treatment. One group of controls was unmedicated, while a second control group received Bacitracin in the feed at 30 g/ton. Results are presented in Table VI.

TABLE VI

| Treatment (ppm) | Average Live Bird Weight (kg) | Feed Conversion |
|---|---|---|
| Control | 2.09 | 1.74 |
| NMBP (1.0) | 2.13 | 1.72 |
| NMBP (2.5) | 2.14 | 1.73 |
| NMBP (5) | 2.08 | 1.75 |
| NMBP (10) | 2.14 | 1.72 |
| NMBP (20) | 2.12 | 1.72 |
| NMBP (40) | 2.10 | 1.75 |
| NMBP (60) | 2.14 | 1.75 |
| Bacitracin MD 30 g/ton | 2.11 | 1.75 |

EXAMPLE XVI

A battery study was conducted in which N-morpholinyl-β-benzoyl-propionamide was administered to chickens in their feed at levels at 2.5 ppm and 5.0 ppm. The control group was unmedicated. Each medicated treatment had 10 replications of 8 birds per replication, with non-medicated controls having 20 replications of 8 birds per replication. Birds were weighed to determine weight gain and feed-to-gain ratio on days 7, 14 and 21. Results are presented in Table VII.

TABLE XVII

| Treatment | Weight Gain (g) | | | Feed Conversion | | | |
|---|---|---|---|---|---|---|---|
| (ppm) | D + 7 | D + 14 | D + 21 | D + 7 | D + 14 | D + 21 | Mortality |
| None | 245 | 507 | 998 | 1.74 | 2.10 | 1.82 | 1.1 |
| NMBP (2.5) | 256 | 526 | 1075 | 1.67 | 1.98 | 1.70 | 1.4 |
| NMBP (5.0) | 262 | 523 | 1027 | 1.65 | 2.02 | 1.71 | .8 |

EXAMPLE XVII

A 70-day study was conducted in which N-morpholinyl-β-benzoyl-propionamide was administered to lambs by i.m. injection or by admixture with feed. In the case of oral administration, the N-morpholinyl-β-benzoyl-propionamide was mixed with the complete mixed ration at a level of 30 ppm. In the case of intramuscular injection, a 2% solution of N-morpholinyl-β-benzoyl-propionamide was administered at a dosage of 1.5 mg/kg, based on body weight, every 2 weeks. Results of the study are presented in Table VIII.

TABLE VIII

| | Treatment | | |
|---|---|---|---|
| Items | Control (Unmedicated) | NMBP Oral | NMBP Injection |
| Number Lambs | 10 | 10 | 9* |
| Weight, kilograms | | | |
| Initial | 29.0 | 28.1 | 27.6 |
| Final | 43.2 | 43.0 | 42.1 |
| Daily Gain, kilograms | | | |
| Period | | | |
| Day 0–14 | .24 | .27 | .23 |
| Day 15–28 | .18 | .20 | .21 |
| Day 29–42 | .27 | .22 | .22 |
| Day 43–56 | .18 | .23 | .22 |
| Day 47–70 | .15 | .14 | .16 |
| Cumulative | | | |
| Day 0–14 | .24 | .27 | .23 |
| Day 0–28 | .21 | .24 | .22 |
| Day 0–42 | .23 | .23 | .22 |
| Day 0–56 | .22 | .23 | .22 |
| Day 0–70 | .20 | .21 | .21 |
| Daily Feed DM Consumption, kilograms | | | |
| Period | | | |
| Day 0–14 | 1.02 | 1.05 | 0.94 |
| Day 15–28 | 1.13 | 1.16 | 1.06 |
| Day 29–42 | 1.20 | 1.17 | 1.14 |
| Day 43–56 | 1.27 | 1.19 | 1.12 |
| Day 57–70 | 1.27 | 1.26 | 1.29 |
| Cumulative | | | |
| Day 0–14 | 1.02 | 1.05 | 0.94 |
| Day 0–28 | 1.08 | 1.10 | 1.00 |
| Day 0–42 | 1.12 | 1.12 | 1.05 |
| Day 0–56 | 1.16 | 1.14 | 1.06 |
| Day 0–70 Feed DM/Gain | 1.18 | 1.16 | 1.11 |
| Period | | | |
| Day 0–14 | 4.25 | 3.89 | 4.09 |
| Day 15–28 | 6.28 | 5.80 | 5.05 |
| Day 29–42 | 4.44 | 5.32 | 5.18 |
| Day 43–56 | 7.06 | 5.17 | 5.09 |
| Day 57–70 | 8.47 | 9.00 | 8.06 |
| Cumulative | | | |
| Day 0–14 | 4.25 | 3.89 | 4.09 |
| Day 0–28 | 5.14 | 4.58 | 4.55 |
| Day 0–42 | 4.87 | 4.87 | 4.77 |
| Day 0–56 | 5.27 | 4.96 | 4.82 |
| Day 0–70 | 5.90 | 5.52 | 5.29 |

*Data from one lamb not included. The lamb was sacrificed on Day 55 of the trial after losing 10 pounds during the previous 2-week period. Necropsy revealed chronic focal pneumonia.

What is claimed is:

1. A method for promoting the growth of swine, poultry, cattle or sheep, which comprises administering to the animal a growth promoting amount on one or more compounds of the formula I

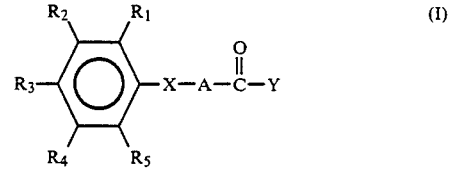

wherein $R_1$, $R_2$, $R_3$, $R_4$ and $R_5$, which can be the same or different, are each selected from the group consisting of hydrogen, alkyl having 1 to 4 carbon atoms, alkoxy having 1 to 4 carbon atoms and halogen;

X is carbonyl;

A is a linear or branched alkylene having from 1 to 8 carbon atoms;

Y is morpholino.

2. A method in accordance with claim 1, wherein each of $R_1$, $R_2$, $R_3$, $R_4$ and $R_5$ is hydrogen; and A is alkylene having 1–2 carbon atoms.

3. A method in accordance with claim 1, wherein the compound is N-morpholinyl-β-benzoyl-propionamide.

4. A method in accordance with claims 1, 2 or 3, wherein the compound is administered parenterally.

5. A method in accordance with claim 1, 2 or 3, wherein the compound is administered orally.

6. A method in accordance with claim 1, 2 or 3, wherein the compound of formula I is administered by admixing it with animal feed.

7. A method in accordance with claim 1, 2, or 3, wherein the compound of formula I is administered to an animal selected from the group consisting of swine, poultry, and sheep.

* * * * *

UNITED STATES PATENT AND TRADEMARK OFFICE
CERTIFICATE OF CORRECTION

PATENT NO. : 4,950,669

DATED : August 21, 1990

INVENTOR(S) : Garzia, et al.

It is certified that error appears in the above-identified patent and that said Letters Patent is hereby corrected as shown below:

Col. 6, line 49, delete "65", and insert therefor --$\gamma$--.

Col. 12, line 47, after "having", delete "I", and insert therefor --1--.

Signed and Sealed this

Eleventh Day of August, 1992

Attest:

DOUGLAS B. COMER

*Attesting Officer*      *Acting Commissioner of Patents and Trademarks*